United States Patent
Huff et al.

(10) Patent No.: US 10,646,354 B2
(45) Date of Patent: May 12, 2020

(54) KIT WITH FEMORAL PROSTHESES HAVING INSERTION/EXTRACTION FEATURES

(71) Applicant: DePuy Synthes Products, Inc., Raynham, MA (US)

(72) Inventors: Daniel N. Huff, Warsaw, IN (US); Ian G. Delaney, Columbia City, IN (US); Joel M. Matta, Malibu, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 140 days.

(21) Appl. No.: 16/028,839

(22) Filed: Jul. 6, 2018

(65) Prior Publication Data

US 2018/0311050 A1 Nov. 1, 2018

Related U.S. Application Data

(63) Continuation of application No. 14/791,960, filed on Jul. 6, 2015, now Pat. No. 10,022,244, which is a
(Continued)

(51) Int. Cl.
*A61F 2/46* (2006.01)
*A61F 2/36* (2006.01)
*A61F 2/30* (2006.01)

(52) U.S. Cl.
CPC ............ *A61F 2/4607* (2013.01); *A61F 2/367* (2013.01); *A61F 2002/30616* (2013.01);
(Continued)

(58) Field of Classification Search
CPC ........... A61F 2/4607; A61F 2002/2825; A61B 17/74; A61B 17/72
(Continued)

(56) References Cited

U.S. PATENT DOCUMENTS 4,919,679 A 4/1990 Averill et al.
4,995,883 A 2/1991 Demane et al.
(Continued)

FOREIGN PATENT DOCUMENTS

EP 0672396 A2 9/1995
FR 2735970 A1 1/1997
(Continued)

OTHER PUBLICATIONS

European Search Report corresponding to European Application No. EP 13186393.8, dated Dec. 11, 2013 (6 pages.).
(Continued)

*Primary Examiner* — David W Bates
(74) *Attorney, Agent, or Firm* — Maginot, Moore & Beck, LLP

(57) ABSTRACT

A kit includes a number of femoral prostheses of different sizes and shapes. Each femoral prostheses in the kit includes a femoral stem including a proximal end portion defining a proximal stem axis, a femoral neck portion including a lateral shoulder extending distally and laterally at an angle relative to the proximal stem axis, such that when projected onto a coronal plane including the proximal stem axis, the lateral shoulder is not parallel to the proximal stem axis. Each prostheses further includes an insertion/extraction cavity extending distally from a proximal surface of the neck portion, the cavity defining an insertion/extraction cavity axis which, when projected on to the coronal plane, is not parallel with the proximal stem axis, and the lateral shoulder of each femoral prosthesis is oriented at an angle relative to the proximal stem axis that is different from the angle of each of the other femoral prostheses.

17 Claims, 6 Drawing Sheets

Related U.S. Application Data continuation of application No. 13/630,333, filed on Sep. 28, 2012, now Pat. No. 9,084,685.

(52) U.S. Cl.
CPC ............... *A61F 2002/4619* (2013.01); *A61F 2002/4629* (2013.01); *A61F 2002/4681* (2013.01); *A61F 2002/4687* (2013.01)

(58) Field of Classification Search
USPC ........................................................ 606/99
See application file for complete search history.

(56) References Cited

U.S. PATENT DOCUMENTS

| | | | |
|---|---|---|---|
| 6,626,913 | B1 | 9/2003 | McKinnon et al. |
| 7,585,301 | B2 | 9/2009 | Santarella et al. |
| 7,935,125 | B2 * | 5/2011 | Bastian ............. A61B 17/1659 606/99 |
| 8,216,238 | B2 * | 7/2012 | Medoff ................. A61B 17/72 606/281 |
| 8,337,504 | B2 | 12/2012 | Surma |
| 9,084,685 | B2 * | 7/2015 | Huff ..................... A61F 2/4607 |
| 2006/0015101 | A1 | 1/2006 | Warburton et al. |
| 2007/0288096 | A1 * | 12/2007 | Surma .................... A61F 2/367 623/22.4 |
| 2008/0172061 | A1 | 7/2008 | Ragbir |
| 2010/0331994 | A1 | 12/2010 | Surma |
| 2011/0009976 | A1 * | 1/2011 | Cruchet ............ A61B 17/1668 623/22.46 |

FOREIGN PATENT DOCUMENTS

| | | |
|---|---|---|
| FR | 2963733 A1 | 2/2012 |
| JP | 2007508063 A | 4/2007 |
| JP | 2008119051 A | 5/2008 |

OTHER PUBLICATIONS

Extended European Search Report corresponding to European application No. EP 16176587.0 dated Nov. 8, 2016 (6 pages).

Translation of Japanese Notification of Reasons for Refusal corresponding to Japanese Patent Application No. 2017-209043, dated Jul. 31, 2018 (4 pages).

* cited by examiner

KIT WITH FEMORAL PROSTHESES HAVING INSERTION/EXTRACTION FEATURES

This is a continuation application of co-pending U.S. application Ser. No. 14/791,960, filed on Jul. 6, 2015, which issued as U.S. patent Ser. No. 10/022,244 on Jul. 17, 2018, which is a continuation of U.S. application Ser. No. 13/630,333, filed on Sep. 28, 2012, which issued as U.S. Pat. No. 9,084,685 on Jul. 21, 2015, the entire disclosures of which are incorporated herein by reference.

FIELD

This disclosure relates generally to femoral prostheses and, more specifically, to features facilitating insertion and extraction of femoral prostheses.

BACKGROUND

Hip arthroplasty can be used to restore function to an injured or diseased hip joint. When performing surgical procedures such as hip arthroplasty, physicians generally attempt to damage as little tissue as possible to minimize trauma to the patient, reducing the time and effort required for the patient's recovery. To facilitate this goal, advances in medical technology have enabled minimally invasive surgical procedures, wherein a minimally necessary number of incisions are made and the incisions are as small as functionally possible. Accordingly, in minimally invasive procedures, the openings through which physicians perform procedures are relatively small, resulting in a limited range of motion and maneuverability for procedural tools and equipment. Thus, minimally invasive procedures provide benefits, such as minimizing trauma to the patient and reducing the patient's recovery, as well as challenges, such as reducing the workspace and range of motion for physicians and their tools during procedures.

For the purposes of surgical procedures, such as hip arthroplasty, positions and directions relative to the hip joint may be described using anatomical directions. Accordingly, as used herein, proximal refers to the direction toward to the hip joint, distal refers to the direction away from the hip joint, anterior refers to the direction toward to the front of the body, posterior refers to the direction toward to the back of the body, medial refers to the direction toward to the centerline of the body and lateral refers to the direction away from the centerline of the body. Additionally, aspects of the hip joint can be described relative to the anatomical planes: the transverse plane, which divides the body into a superior portion (nearer to the head) and an inferior portion (nearer to the feet); the sagittal plane, which divides the body into a left portion and a right portion; and the coronal plane, which divides the body into the anterior portion and the posterior portion.

In a total hip arthroplasty, both the "ball" and the "socket" of the hip joint are replaced with prosthetic device implants to form a new joint. The ball of the hip joint is often replaced by removing the femoral head from the proximal end of the femur, inserting a femoral prosthesis partially into the intramedullary canal of the femur, and coupling a ball to the proximal end of the femoral prosthesis. The socket of the hip joint is often replaced by removing bone from the acetabulum to create a cup-shaped opening and inserting an acetabular cup prosthesis into the cup-shaped opening. In a partial hip arthroplasty, either the ball or the socket of the hip joint may be replaced with a prosthetic device. If, after a total or partial hip arthroplasty, a subsequent medical event arises involving one of the hip implant prostheses, a procedure may be required to extract or remove the implanted prosthetic device to enable replacement with another prosthesis.

Inserting and extracting a femoral prosthetic device from a patient's femur generally require specific tools which engage with the femoral prosthetic device and enable a physician to apply sufficient force to the femoral prosthetic device. Because a tight fit between the femoral prosthetic device and existing femoral bone is desired, both insertion and extraction of a femoral prosthetic device generally requires application of a significant impact force to the femoral prosthetic device. Such an impact force is usually applied to an impact surface on the tool. The impact force is transferred through the tool to the femoral prosthetic device.

Due to the anatomy of the hip joint and the reduced range of maneuverability in minimally invasive hip arthroplasties, the tools for insertion and extraction are generally curved, like that in FIG. 1, to accommodate available access angles and to avoid unwanted contact with and impingement of bones and tissues during the procedures. The curved shapes of the tools, while providing some benefits, in turn present additional challenges and difficulties during insertion and removal of femoral prosthetic devices.

As shown in FIG. 1, for example, because the tool 10 is curved, the impact force $F_I$ applied to the impact surface 12 by the physician is offset from the transfer location 14 where the force is applied to the femoral prosthetic device through the tool 10. One problem that arises as a result of this offset 16 is the generation of a moment M about the transfer location 14. In other words, application of the impact force $F_I$ at the impact surface 12 generates a tendency for the tool 10 to rotate about the transfer location 14. Accordingly, to prevent the tool 10 from rotating about the transfer location 14 and maintain stability of the tool 10 during the procedure, the physician must apply a manual force $F_M$ to the tool 10 to oppose the moment M generated by the impact force $F_I$.

By way of example, if the offset 16 between the axis of the impact force $F_I$ and the transfer location 14 is 50 mm and the physician grips the tool 10 at a gripping offset 22 that is 230.7 mm from the transfer location 14, the moment M generated at the transfer location 14 has a magnitude that is approximately ⅕ the magnitude of the impact force $F_I$. Accordingly, to oppose the moment M, the physician must apply a manual force $F_M$ that is approximately ⅕ the magnitude of the impact force $F_I$. If the impact force $F_I$ is, for example, 500 lbf, a physician has to apply a manual force $F_M$ that is approximately 100 lbf while also maintaining proper positioning of the instruments.

Another problem that arises due to the generated moment M is that the tip 18 of the tool 10 which engages the femoral prosthetic device at the transfer location 14 can be sheared off, becoming lodged in the femoral prosthetic device. As noted above, to counteract the moment M generated by the impact force $F_I$ applied to the tool 10, physicians must apply a sufficient opposing manual force $F_M$. Instead of applying the manual force $F_M$ to oppose the moment M, however, some physicians have intuitively attempted to eliminate the moment M by hitting the edge of the impact surface 12, thereby applying the impact force $F_I$ at an angle 20 relative to the impact surface 12. By applying the impact force $F_I$ to the tool 10 at an angle 20, however, the physician generates a significant shear stress $F_S$ on the tip 18 of the tool 10 which engages the femoral prosthetic device. The shear stress $F_S$ has resulted in shearing off the tip 18 of the tool 10, requiring additional corrective measures to be undertaken during the procedure.

Given the above discussion, it would be advantageous to provide an improved femoral prosthesis including features enabling insertion/extraction with greater efficiency and less risk for error. It would also be advantageous to provide an improved insertion/extraction tool including features enabling insertion/extraction with greater efficiency and less risk for error. It would also be advantageous to provide an improved method for inserting/extracting femoral prosthetic devices with greater efficiency and less risk for error.

SUMMARY

In accordance with one embodiment of the disclosure, there is provided a femoral prosthesis including a stem and a neck portion. The stem includes a proximal end portion which defines a proximal stem axis. The neck portion is located proximally of the proximal end portion. The neck portion includes a proximal surface and an insertion/extraction cavity extends distally from the proximal surface. The insertion/extraction cavity is configured to couple with an insertion/extraction instrument. The insertion/extraction cavity defines an insertion/extraction instrument coupling axis which, when projected onto a coronal plane including the proximal stem axis, is not parallel with the proximal stem axis.

In accordance with another embodiment of the disclosure, there is provided a femoral prosthesis system including a femoral prosthesis and an insertion/extraction instrument. The femoral prosthesis includes a femoral stem and a neck portion. The femoral stem has a proximal end portion which defines a proximal stem axis. The neck portion is located proximally of the proximal end portion. The neck portion includes a proximal surface and an insertion/extraction cavity extends distally from a proximal surface. The insertion/extraction cavity defines an insertion/extraction instrument coupling axis which, when projected onto a coronal plane including the proximal stem axis, is not parallel with the proximal stem axis. The insertion/extraction instrument includes a distal end portion configured to couple with the insertion/extraction cavity.

In accordance with yet another embodiment of the disclosure, there is provided a method of inserting a femoral prosthesis including coupling an insertion/extraction instrument to the femoral prosthesis, inserting a distal end portion of the femoral prosthesis into a femur, and impacting a proximal end portion of the insertion/extraction instrument. The instrument includes a body defining a longitudinal axis and the femoral prosthesis includes a proximal portion and a stem portion defining a longitudinal axis. Coupling the insertion/extraction instrument to the femoral prosthesis includes coupling the instrument with the proximal portion of the femoral prosthesis such that the longitudinal axis of the body of the instrument is not parallel with the longitudinal axis of the stem portion of the femoral prosthesis.

In another embodiment, a method of inserting a femoral prosthesis includes coupling an insertion/extraction instrument with an insertion/extraction cavity of a femoral component using a threaded member, the insertion/extraction cavity defining a cavity axis which is not parallel with a longitudinal axis defined by a proximal stem portion of the femoral prosthesis, inserting a distal end portion of the femoral prosthesis into a femur, impacting a proximal end portion of the insertion/extraction instrument, and transferring an impact force from the proximal end portion to the femoral prosthesis through the threaded member.

In one or more of the foregoing embodiments, coupling the insertion/extraction instrument with the insertion/extraction cavity includes rotating the proximal end portion of the insertion/extraction instrument thereby causing rotation of the threaded member.

In one or more of the foregoing embodiments, transferring the impact force includes transferring the impact force through a shaft extending between the proximal end portion and the threaded member.

In one or more of the foregoing embodiments, the shaft defines a shaft axis, and coupling the insertion/extraction instrument with the insertion/extraction cavity includes inserting the threaded member into the insertion/extraction cavity with the shaft axis aligned with the cavity axis.

In one or more of the foregoing embodiments, coupling the insertion/extraction instrument with the insertion/extraction cavity includes inserting a first alignment feature of the insertion/extraction instrument into a second alignment feature of the insertion/extraction cavity with the shaft axis aligned with the cavity axis.

In one or more of the foregoing embodiments, rotating the proximal end portion of the insertion/extraction instrument causes rotation of the shaft within a housing.

In one or more of the foregoing embodiments, the housing defines a housing axis, and coupling the insertion/extraction instrument with the insertion/extraction cavity includes inserting the threaded member into the insertion/extraction cavity with the housing axis aligned with the cavity axis.

In one or more of the foregoing embodiments, coupling the insertion/extraction instrument with the insertion/extraction cavity of a femoral component includes forcing a portion of the housing against the femoral prosthesis by rotation of the threaded member.

In one or more of the foregoing embodiments, forcing the portion of the housing against the femoral prosthesis includes forcing the first alignment feature against a portion of the second alignment feature.

The above described features and advantages, as well as others, will become more readily apparent to those of ordinary skill in the art by reference to the following detailed description and accompanying drawings. While it would be desirable to provide a femoral prosthesis and femoral prosthesis system that provides one or more of these or other advantageous features, the teachings disclosed herein extend to those embodiments which fall within the scope of the appended claims, regardless of whether they accomplish one or more of the above-mentioned advantages.

BRIEF DESCRIPTION OF THE DRAWINGS

Features of the femoral prosthesis and the femoral prosthesis system are apparent to those skilled in the art from the following detailed description with reference to the following drawings.

DETAILED DESCRIPTION

Figure 1:
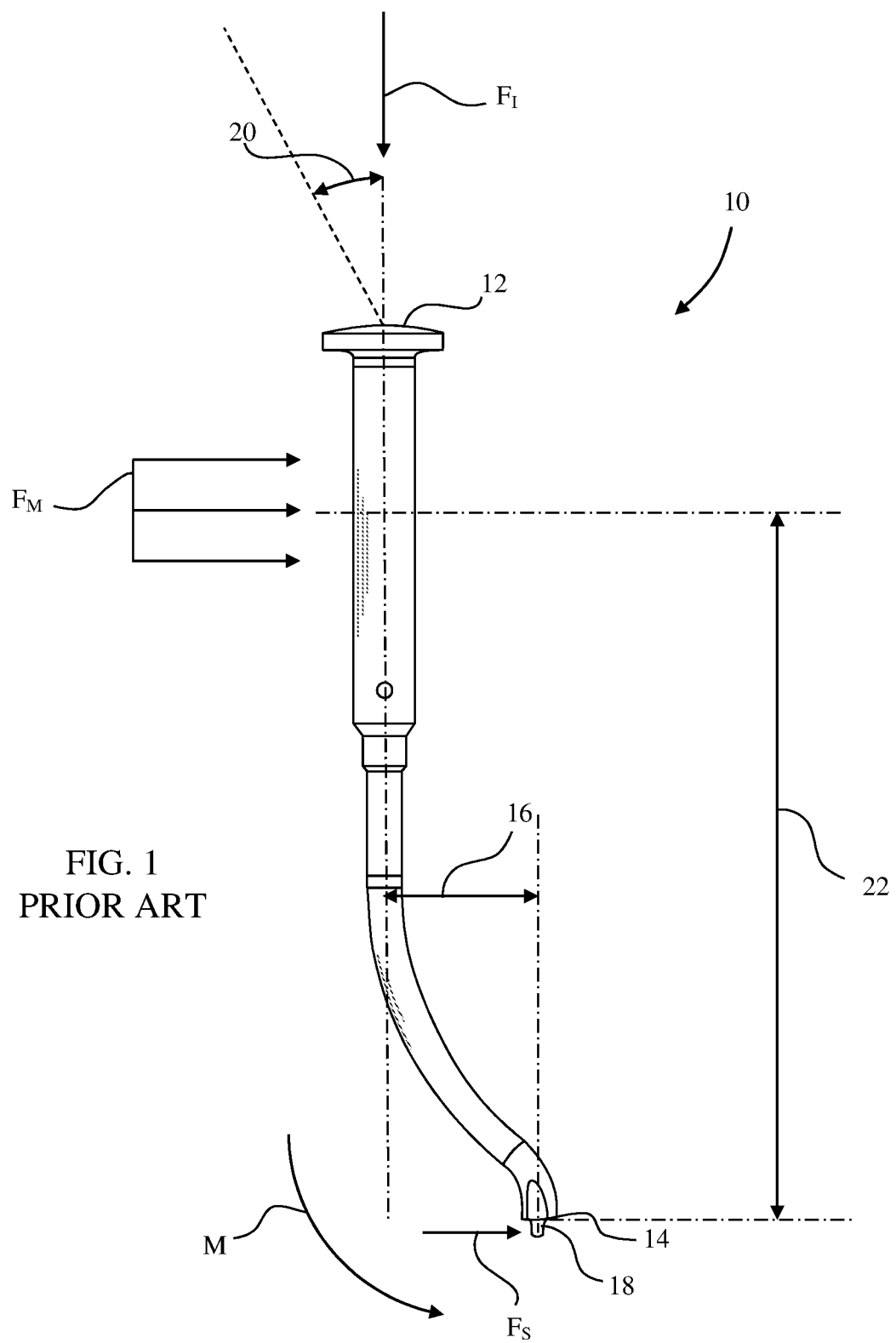
FIG. 1 depicts a side plan view of a prior art tool used to transfer an applied force to a femoral prosthesis during a hip arthroplasty procedure.
Figure 2:
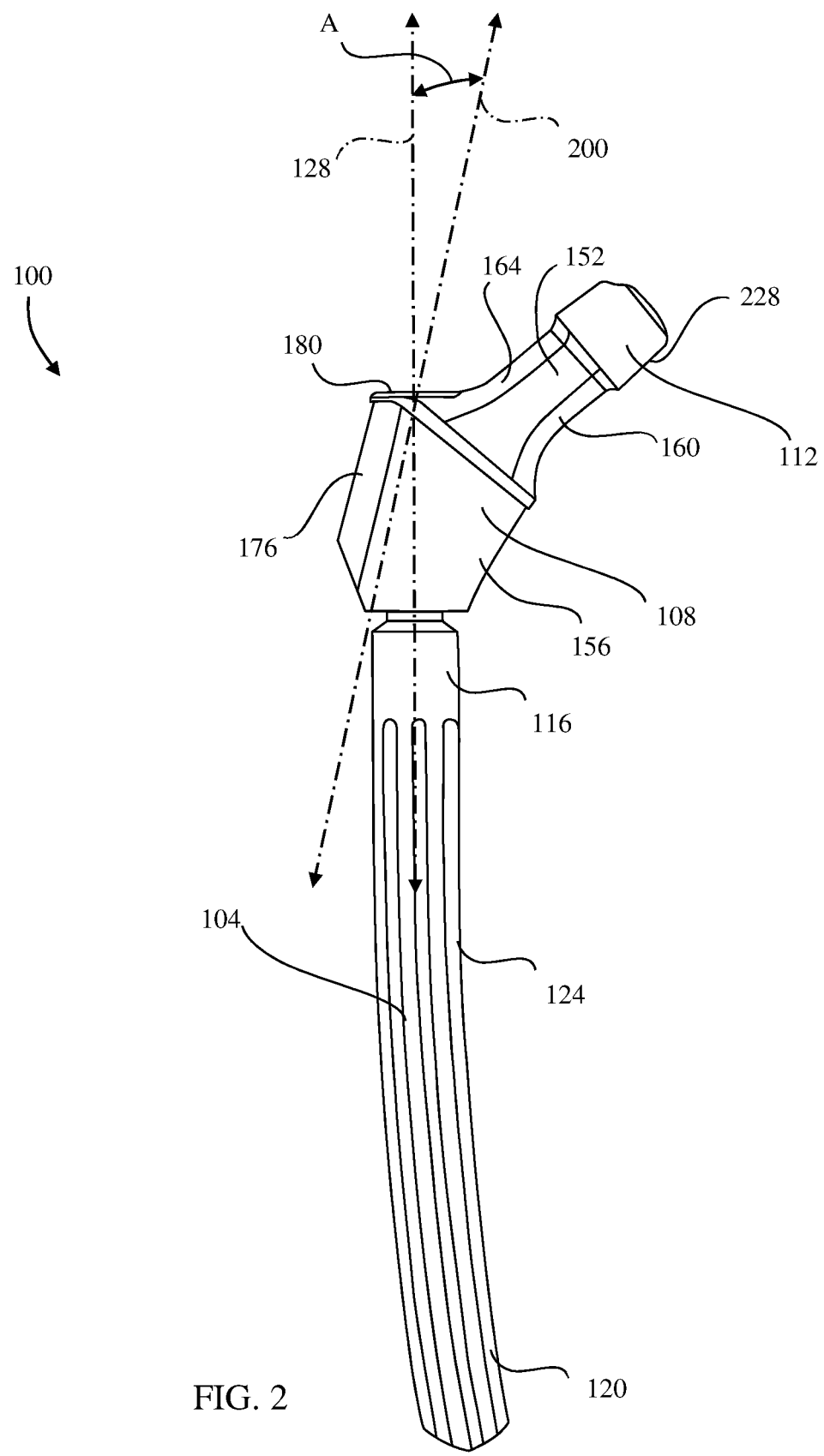
FIG. 2 depicts a side plan view of a femoral prosthesis to be used in hip replacement.

As shown in FIG. 2, the femoral prosthesis 100 includes a stem 104, a neck portion 108, and a femoral head fitting 112. The neck portion 108 extends proximally from the stem 104 and the femoral head fitting 112 extends proximally from the neck portion 108. The stem 104, neck portion 108, and femoral head fitting 112, in one embodiment, are formed from one piece of material and, in another embodiment, are formed from individual pieces of material that are subsequently coupled together.

The stem 104 includes a stem proximal end portion 116, a stem distal end portion 120 and a stem body portion 124. The stem 104 is constructed out of a metal or alloy, such as for example, a titanium alloy, or another material known in the art to have similar properties desirable for long term implantation into the femur. The stem 104 is substantially straight along the stem body portion 124 from the stem proximal end portion 116 to the stem body portion 124. The stem proximal end portion 116 defines a longitudinal axis, referred to herein as a proximal stem axis 128, extending axially through the approximate center of the stem proximal end portion 116. When the stem proximal end portion 116 is projected onto a transverse plane, the proximal stem axis 128 extends in a direction substantially perpendicular to the transverse plane.

The stem body portion 124 extends between the stem proximal end portion 116 and the stem distal end portion 120 and has a generally elongated shape. The stem body portion 124 in one embodiment includes a taper such that the stem body portion 124 is smaller nearer to the stem distal end portion 120 and larger nearer to the stem proximal end portion 116. The taper is sized and configured to facilitate insertion of the femoral prosthesis 100 into an intermedullary canal of a femur.

The neck portion 108 extends proximally from the stem proximal end portion 116 and includes a neck proximal end portion 152, a neck distal end portion 156, a neck medial portion 160 and a neck lateral portion 164. The neck medial portion 160 and the neck lateral portion 164 extend between the neck proximal end portion 152 and the neck distal end portion 156 and are arranged opposite one another along the neck portion 108. The neck lateral portion 164 includes a shoulder 176. In particular, the neck portion 108 is shaped such that the neck lateral portion 164 is more medial at the neck proximal end portion 152 than at the neck distal end portion 156 forming the shoulder 176.

The neck distal end portion 156 is located adjacent to the stem proximal end portion 116 and the neck proximal end portion 152 extends proximally from the neck distal end portion 156. The neck proximal end portion 152 includes a proximal surface 180 extending along at least a portion of the neck proximal end portion 152 and the neck lateral portion 164. The proximal surface 180 is oriented such that it substantially faces proximally away from the stem 104 and the neck portion 108. Additionally, when the neck proximal end portion 152 is viewed in a transverse plane, the proximal surface 180 is substantially parallel to the transverse plane.

Figure 3:
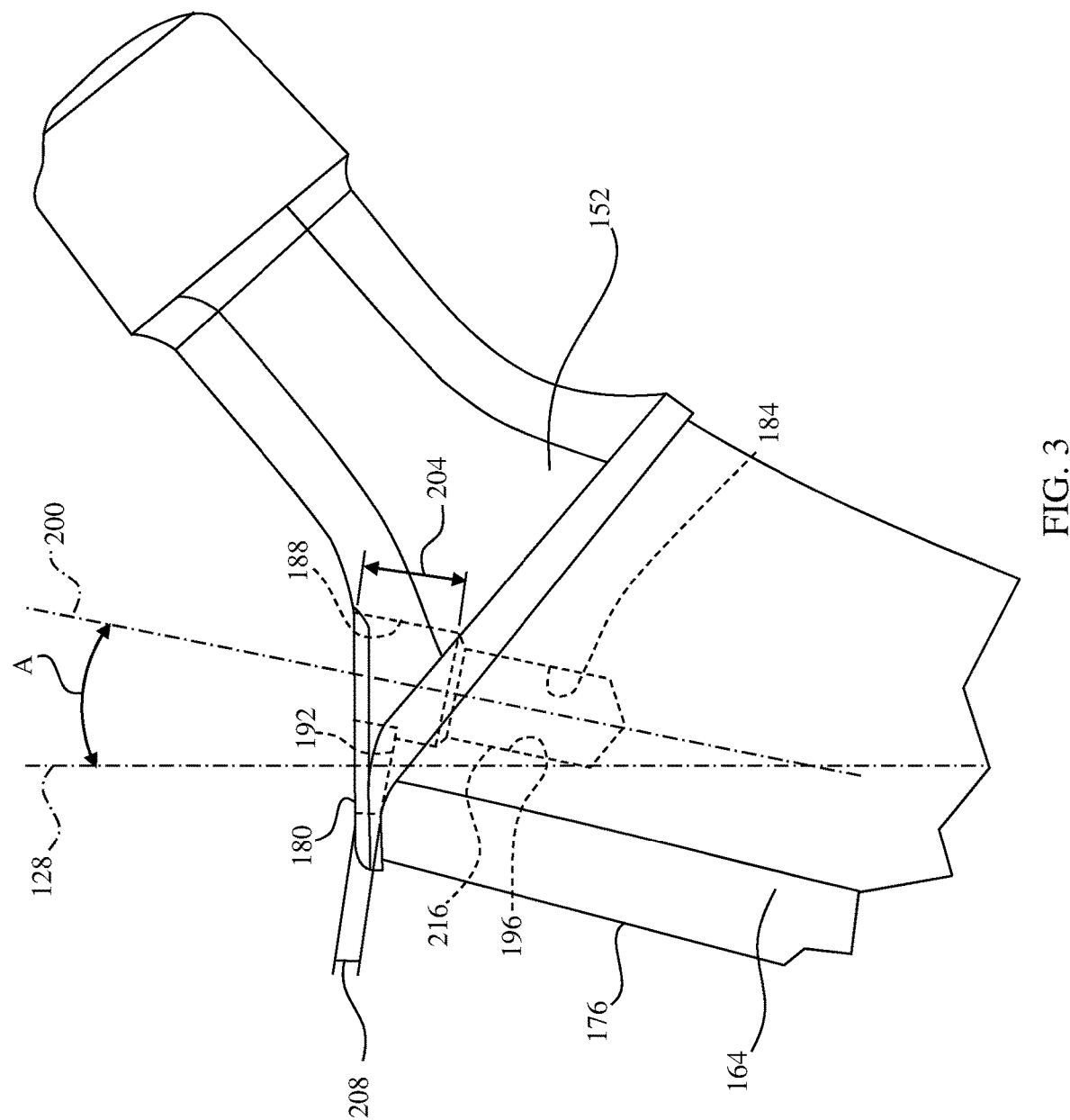
FIG. 3 depicts a fragmentary side plan view of the femoral prosthesis of FIG. 2, wherein a proximal portion of the femoral prosthesis is shown for clarity.

The neck proximal end portion 152 also includes an insertion/extraction cavity 184 extending distally into the proximal surface 180 as shown in FIG. 3. The insertion/extraction cavity 184 includes an insertion/extraction cavity axis 200. The insertion/extraction cavity 184 extends distally into the proximal surface 180 at an angle A that is not orthogonal to the proximal surface 180. In particular, as described in more detail below, as the insertion/extraction cavity 184 extends distally, it also extends laterally.

Figure 4:
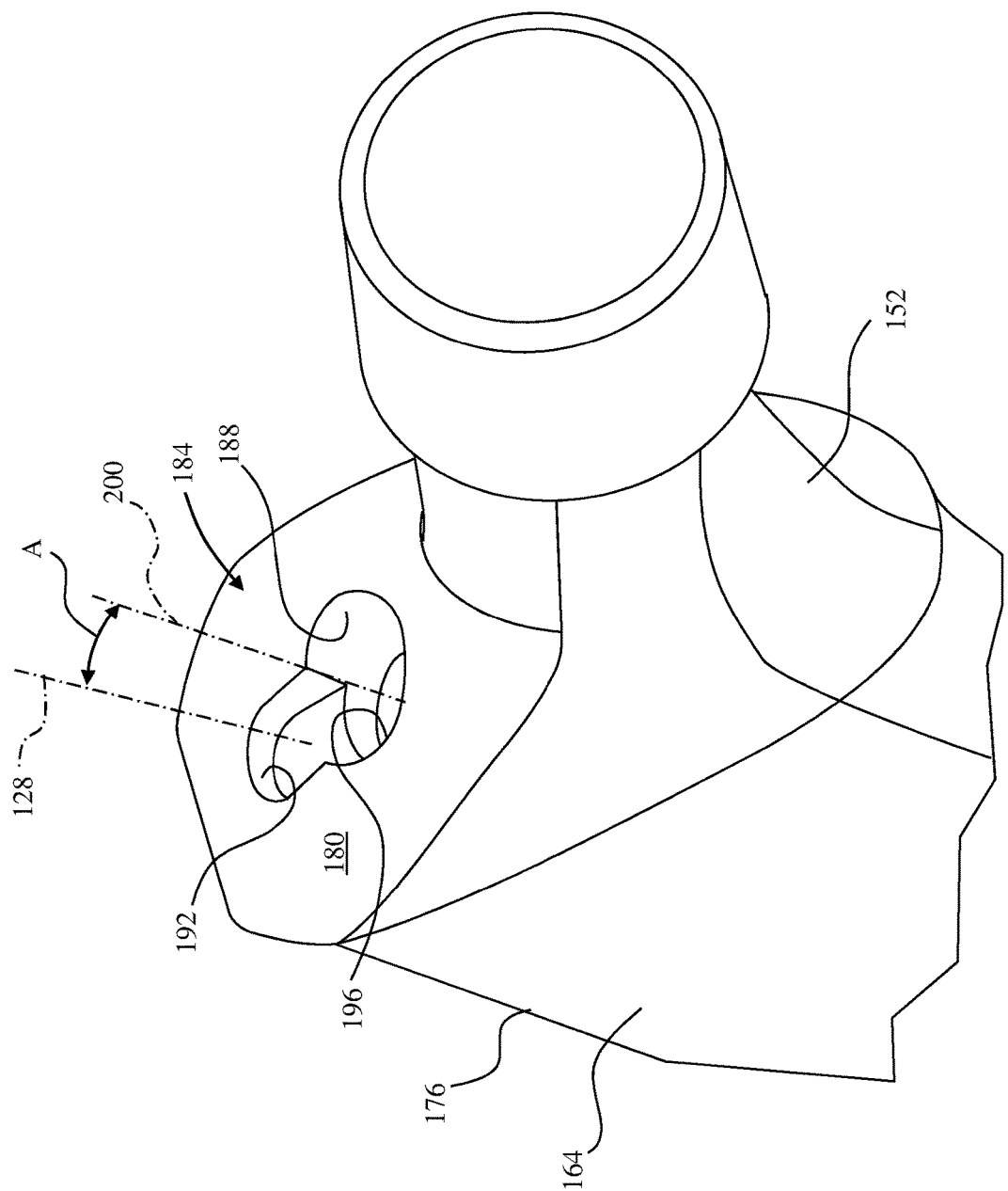
FIG. 4 depicts a fragmentary top perspective view of the femoral prosthesis of FIG. 2, wherein a proximal portion of the femoral prosthesis is shown for clarity.

With reference to FIG. 3 and FIG. 4, the neck proximal end portion 152 and the insertion/extraction cavity 184 are described in more detail. As shown, the insertion/extraction cavity 184 includes an instrument receiving portion 188, a prosthesis keyed portion 192, and a prosthesis threaded portion 196. The instrument receiving portion 188 is located directly distally to the proximal surface 180 and is open to the proximal surface 180. The instrument receiving portion 188 has an instrument receiving portion depth 204 (shown in FIG. 3) defined relative to the proximal surface 180. The instrument receiving portion 188, in this embodiment, is also in open communication with both the prosthesis keyed portion 192 and the prosthesis threaded portion 196. In some embodiments, however, the instrument receiving portion 188 is not in open communication with the prosthesis keyed portion 192.

The prosthesis keyed portion 192 is also located directly distally to the proximal surface 180 and is open to the proximal surface 180. The prosthesis keyed portion 192 has a prosthesis keyed portion depth 208 (shown in FIG. 3) defined relative to the proximal surface 180, and the prosthesis keyed portion depth 208 is shallower than the instrument receiving portion depth 204. The prosthesis keyed portion 192 is offset laterally from the instrument receiving portion 188.

The prosthesis threaded portion 196 extends distally from the instrument receiving portion 188. The prosthesis threaded portion 196 (shown in FIG. 3) is defined by a wall 216. The prosthesis threaded portion 196 includes threads (not shown) extending into the wall 216.

The insertion/extraction cavity axis 200 extends axially through the center of the instrument receiving portion 188 and the prosthesis threaded portion 196 (shown in FIG. 3) of the insertion/extraction cavity 184. In other embodiments, however, the insertion/extraction cavity axis 200 need not extend through the center of the instrument receiving portion 188. When the insertion/extraction cavity axis 200 and the proximal stem axis 128 are projected onto a coronal plane, the insertion/extraction cavity axis 200 is not oriented in a direction that is substantially parallel to the proximal stem axis 128 but instead extends at the angle A relative to the proximal stem axis 128. In particular, the insertion/extraction cavity axis 200 extends at the angle A proximally and medially to the proximal stem axis 128. In at least one embodiment, the angle A is in the range of approximately one through approximately forty-five degrees. The angle A in one embodiment is twelve degrees relative to the proximal stem axis 128.

In one embodiment, the insertion/extraction cavity 184 is oriented in a direction that is approximately parallel to the shoulder 176. As noted above, the shoulder 176 is formed due to the neck lateral portion 164 extending more medially at the neck proximal end portion 152 than at the neck distal end portion 156 (shown in FIG. 2). In other words, the shoulder 176 extends laterally as it extends distally relative to the proximal surface 180. Accordingly, when the stem 104 and the neck portion 108 (shown in FIG. 2) are viewed in the coronal plane, the shoulder 176 is not oriented in a direction that is substantially parallel to the proximal stem axis 128 but instead extends at an angle A relative to the proximal stem axis 128.

In one embodiment, there is provided a kit including a plurality of femoral prostheses of different sizes and shapes allowing the physician to select the best fitting prosthesis from the kit to insert into a particular patient's femur. The best fitting prosthesis is determined by, among other considerations, the morphology and topography of the patient's femur. Accordingly, to provide a useful range of fits, each femoral prosthesis in the kit has a shoulder 176 oriented at an angle A relative to the proximal stem axis 128 that is different than the angle of each of the other femoral prostheses in the kit. In this embodiment, the angle of the insertion/extraction cavity 184 relative to the proximal stem axis 128 of each of the femoral prostheses in the kit is approximately equal to the angle of the shoulder 176 relative to the proximal stem axis 128 of the smallest femoral prosthesis in the kit. In this embodiment, the angle of the shoulder 176 relative to the proximal stem axis 128 of the smallest femoral prosthesis in the kit is approximately twelve degrees. An advantage of this embodiment is that the physician has the same feel, and exerts the same forces in the same directions, while inserting any of the femoral prostheses into the patient's femur (as described below), because the insertion/extraction cavity 184 is oriented at the same angle regardless of the size or shape of the particular prosthesis. In another embodiment, the angle of the insertion/extraction cavity 184 relative to the proximal stem axis 128 of each of the femoral prostheses in the kit is approximately equal to the angle of the shoulder 176 of that femoral prosthesis relative to the proximal stem axis 128.

Returning to FIG. 2, the femoral head fitting 112 extends proximally from the neck proximal end portion 152 and includes a coupling surface 228 extending around the femoral head fitting 112 and tapering inwardly such that the femoral head fitting 112 is configured to mate for a friction fit with a complementary taper of a ball portion (not shown). Taken together, the femoral prosthesis 100 and the ball portion complete a femoral implant that is used to replace the femoral head of a patient during hip arthroplasty.

Figure 5:
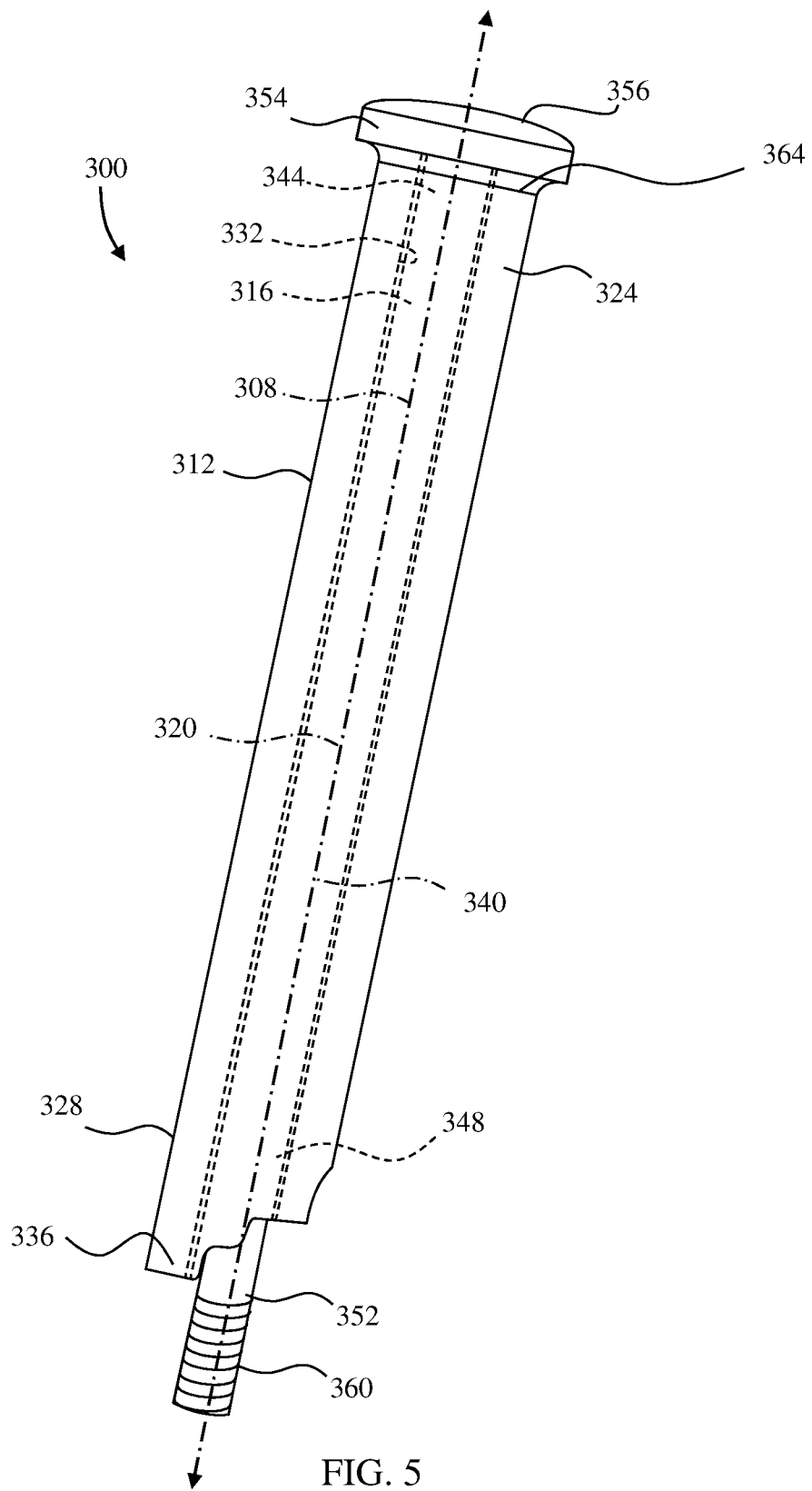
FIG. 5 depicts a side plan view of an insertion/extraction instrument to be used to insert or extract the femoral prosthesis of FIG. 2.

Turning now to FIG. 5, an instrument 300 is provided that is configured to enable insertion of the femoral prosthesis 100, described above and shown in FIG. 2, into and removal of the femoral prosthesis 100 from a patient's femur during hip arthroplasty. The instrument 300 includes an instrument body or housing 312 and a shaft 316. The housing 312 defines a housing axis 320 and includes a housing impact end portion 324, a housing engagement end portion 328, a longitudinal opening 332, and an instrument keyed portion 336. The housing axis 320 extends axially through the center of the housing 312 through the housing impact end portion 324 and the housing engagement end portion 328 and, in this embodiment, is coincident with an impact axis 308. The impact axis 308 is the axis along which force is transferred to a femoral prosthesis such as the femoral prosthesis 100. In another embodiment, however, the housing axis 320 need not be coincident with the impact axis 308.

The housing impact end portion 324 is arranged opposite the housing engagement end portion 328. The longitudinal opening 332 extends through the housing 312 along the housing axis 320 from the housing impact end portion 324 to the housing engagement end portion 328. The instrument keyed portion 336 is located at the distal end of the housing engagement end portion 328.

The shaft 316 defines a shaft axis 340 and includes a shaft impact end portion 344, and a shaft engagement end portion 348, which includes an instrument threaded portion 352. The shaft axis 340 extends axially through the center of the shaft 316 through the shaft impact end portion 344 and the shaft engagement end portion 348. The shaft 316 is sized and configured to be rotatably received and retained within the longitudinal opening 332 of the housing 312 such that the shaft axis 340 is coincident with the housing axis 320. In this embodiment, the shaft axis 340 is, consequently, also coincident with the impact axis 308. In another embodiment, however, the shaft axis 340 need not be coincident with the impact axis 308. When the shaft 316 is received within the housing 312, the shaft impact end portion 344 is adjacent the housing impact end portion 324, the shaft engagement end portion 348 is adjacent the housing engagement end portion 328, and the shaft 316 is rotatable relative to the housing 312.

The shaft impact end portion 344 includes a knob 354 having an impact surface 356. The knob 354 of the shaft impact end portion 344 extends outwardly of housing impact end portion 324 such that the knob 354 protrudes beyond the housing impact end portion 324. The knob 354 is operably connected to the shaft impact end portion 344 and is configured to be gripped. The shaft 316 can be rotated relative to the housing 312 by rotating the knob 354 where it protrudes beyond the housing impact end portion 324. The impact surface 356 is arranged proximally on the knob 354 such that it aligns with and is substantially orthogonal to the shaft axis 340. Accordingly, an impact applied to the impact surface 356 is transferred through the shaft 316 along the shaft axis 340.

The instrument threaded portion 352 protrudes from the housing engagement end portion 328 such that the threads 360 of the instrument threaded portion 352 are exposed. The instrument threaded portion 352 is substantially aligned with the shaft axis 340. As mentioned above, the shaft 316 is configured such that, when the knob 354 on the shaft impact end portion 344 is rotated, the shaft engagement end portion 348 is also rotated, thereby rotating the instrument threaded portion 352 relative to the housing engagement end portion 328.

Figure 6:
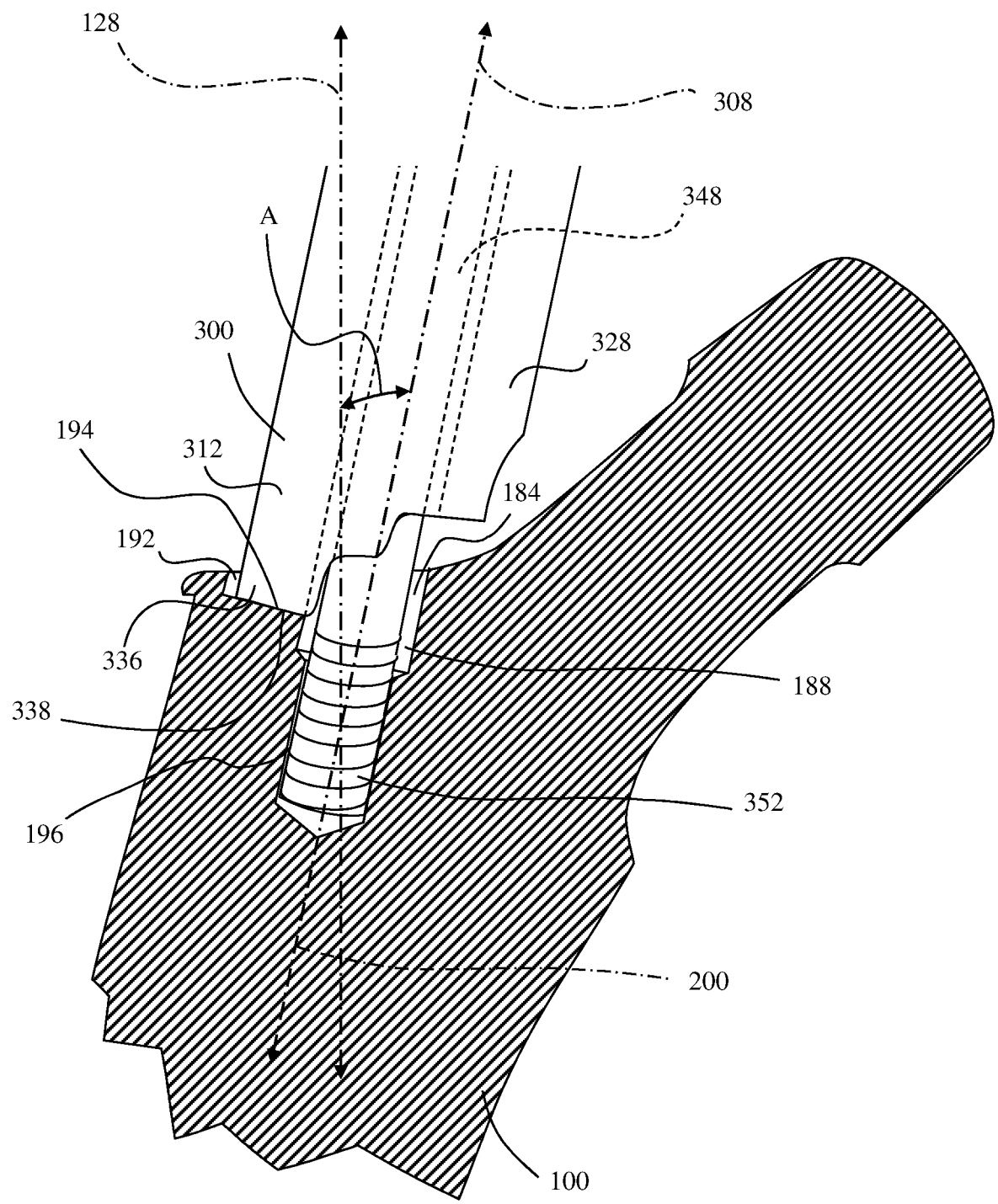
FIG. 6 depicts a cross-sectional view of the side of the femoral prosthesis of FIG. 2, wherein a proximal portion of the femoral prosthesis is shown for clarity, with a fragmentary side plan view of the insertion/extraction instrument of FIG. 5, wherein a distal portion of the insertion/extraction instrument is shown for clarity.

As shown in FIG. 6, the instrument 300 is arranged and configured such that the housing engagement end portion 328 and the shaft engagement end portion 348 engage the insertion/extraction cavity 184 of the femoral prosthesis 100 to facilitate insertion of the femoral prosthesis 100 into a patient's femur and removal of the femoral prosthesis 100 from a patient's femur during hip arthroplasty. In particular, the prosthesis keyed portion 192 is configured to couple with the instrument keyed portion 336, and the prosthesis threaded portion 196 is configured to couple with the instrument threaded portion 352.

In operation, to use the instrument 300 to facilitate insertion of the femoral prosthesis into a patient's femur, the instrument threaded portion 352 is first inserted into the instrument receiving portion 188 to generally align the instrument 300 with the insertion/extraction cavity 184. Once the threaded portion has been received within the instrument receiving portion 188, the instrument keyed portion 336 is inserted into the prosthesis keyed portion 192 to maintain the alignment of the instrument 300 with the femoral prosthesis 100.

Next, the instrument threaded portion 352 is rotated relative to the housing 312 by rotating the knob 354 on the shaft impact end portion 344 (shown in FIG. 5). Because the instrument keyed portion 336 is mated with the prosthesis keyed portion 192, the housing 312 is prevented from rotating relative to the femoral prosthesis 100. Accordingly, when the instrument threaded portion 352 is rotated relative to the housing 312, the instrument threaded portion 352 is also rotated relative to the femoral prosthesis 100. Thus, the instrument threaded portion 352 extends into and threadably engages the prosthesis threaded portion 196 in the insertion/extraction cavity 184. In this embodiment, engagement of the instrument threaded portion 352 with the prosthesis threaded portion 196 couples the instrument 300 with the femoral prosthesis 100 such that the instrument 300 is restricted in movement away from the femoral prosthesis 100. In another embodiment, threaded portions need not be used to couple the instrument 300 with the femoral prosthesis 100, but the instrument 300 is coupled to the femoral prosthesis 100 in another way which restricts movement of the instrument 300 away from the femoral prosthesis 100. For example, either a collet or a bayonet clasp is used to couple the instrument 300 with the femoral prosthesis 100 in such a way as to restrict movement of the instrument 300 away from the femoral prosthesis 100.

Once the instrument threaded portion 352 has fully engaged the prosthesis threaded portion 196, the impact axis 308 is substantially coincident with the insertion/extraction cavity axis 200. Accordingly, because the insertion/extraction cavity axis 200 is not oriented in a direction that is substantially parallel to the proximal stem axis 128 but instead extends at an angle A relative to the proximal stem axis 128, the impact axis 308 also is not parallel with the proximal stem axis 128. An advantage of orienting the impact axis 308 at an angle A relative to the proximal stem axis 128 is that the physician can avoid unnecessary interference with the patient's musculoskeletal system in the hip joint. Because the impact axis 308 is oriented at an angle A, the physician need not have an orthogonal line of access relative to the femoral prosthesis 100 to insert or remove the femoral prosthesis. The most effective combination of leverage and access is achieved by orienting the impact axis 308 at an angle A that is in a range of approximately one degree through approximately forty-five degrees relative to the proximal stem axis 128.

An impact is then applied to the instrument 300 and transferred through the instrument 300 to the attached femoral prosthesis 100. More specifically, when an impact force is applied to the impact surface 356 (shown in FIG. 5), the impact force is transferred through the impact surface 356, the knob 354, the shaft 316, and the threaded portion 352, successively, to the femoral prosthesis 100, thereby facilitating insertion of the femoral prosthesis 100 into the patient's femur. Because the impact axis 308 is coincident with the insertion/extraction cavity axis 200, the impact force is transferred fully and directly into the femoral prosthesis 100 without generating a moment around the instrument threaded portion 352 or applying shear stress to the instrument threaded portion 352. Accordingly, using the instrument 300 in combination with the femoral prosthesis 100 during hip arthroplasty facilitates the insertion of the femoral prosthesis 100 into the patient's femur with more efficiency and less risk for error.

In one embodiment, the housing 312 includes internal threads (not shown) such that when the instrument threaded portion 352 is rotated relative to the housing 312, the shaft 316 travels axially within the housing 312. Accordingly, increasing engagement of the instrument threaded portion 352 with the prosthesis threaded portion 196 causes the shaft 316 to travel distally within the housing 312. Distal movement of the shaft 316 within the housing 312 is limited by contact of the knob 354 on the shaft impact end portion 344 (shown in FIG. 5) with a housing proximal surface 364 on the housing impact end portion 324. In this embodiment, an impact force applied to the impact surface 356 is transferred to the femoral prosthesis 100 through the housing 312 in addition to the shaft 316.

Additionally, in this embodiment, to facilitate the transfer of the impact force to the femoral prosthesis 100 through the housing 312, the instrument keyed portion 336 is configured to contact the prosthesis keyed portion 192. Specifically, an instrument keyed portion surface 338 is configured to contact and rest flatly on a prosthesis keyed portion surface 194. The prosthesis keyed portion surface 194 is arranged substantially orthogonally relative to the insertion/extraction cavity axis 200. When an impact force is applied to the impact surface 356 (shown in FIG. 5), the impact force is transferred through the impact surface 356, the knob 354, the housing proximal surface 364, the instrument keyed portion 336, and, ultimately, the instrument keyed portion surface 338, successively. The arrangement of the prosthesis keyed portion surface 194 relative to the insertion/extraction cavity axis 200 (and thus relative to the impact axis 308) causes the impact force to be transmitted through the instrument keyed portion 336 to the femoral prosthesis 100 in a direction along the instrument keyed portion 336 such that neither the instrument threaded portion 352 nor the instrument keyed portion 336 experiences any shear stress. The transfer of the impact force to the femoral prosthesis 100, thereby further facilitates insertion of the femoral prosthesis 100 into the patient's femur with greater efficiency and less risk for error.

In embodiments wherein the instrument 300 is used only for insertion, through the processes described above, the threaded portions 196 and 352 may be omitted. In an embodiment wherein the instrument 300 does not include threaded portions 196 and 352, the shaft engagement end portion 348 is used solely for alignment and the only area of contact between the instrument 300 and the femoral prosthesis 100 is where the instrument keyed portion surface 338 contacts the prosthesis keyed portion surface 194. Put another way, the impact is transferred to the femoral prosthesis 100 only through the housing 312 of the instrument 300.

In embodiments wherein the threaded portions 196 and 352 are included, however, the instrument 300 may be used for extracting, in addition to inserting, the femoral prosthesis 100. Specifically, the threaded portions 196 and 352 of the prosthesis and the instrument, respectively, enable use of the prosthesis 100 and the instrument 300 for extraction from the femur in addition to insertion into the femur. The process by which the instrument 300 is used for insertion of the prosthesis 100 is described above. The process by which the instrument 300 is used for extraction of the prosthesis 100 differs from the insertion process in that the threaded portions 196 and 352 engage with one another, such that applying force to the instrument 300 in a direction away from the prosthesis 100 will pull the prosthesis 100 away from the femur, thereby extracting the prosthesis 100 from the intermedullary canal.

By way of example, the instrument 300, in some embodiments, includes features that enable the impact force to be applied in the opposite direction relative to the insertion impact. In particular, the instrument 300 is configured such that the knob 354 aligns with and is substantially orthogonal to the shaft axis 340 such that an impact applied to the underside of the knob 354 is transferred through the shaft 316 along the shaft axis 340. Alternatively, the housing 312 includes a flange (not shown) which extends outwardly from the housing axis 320 at the shaft impact end portion 344 and is configured to receive an impact applied in a direction away from the shaft engagement end portion 348. In this way, the instrument 300 is still used with the femoral prosthesis 100 but, because the impact is applied in the opposite direction, the instrument 300 facilitates extraction of, rather than insertion of, the femoral prosthesis 100. Accordingly, using the instrument 300 in combination with the femoral prosthesis 100 during hip arthroplasty facilitates the extraction of the femoral prosthesis 100 from the patient's femur with more efficiency and less risk for error.

Consequently, while the instrument 300 in FIG. 5 is configured to both insert and extract a femoral prosthesis 100, in some embodiments, a separate instrument is used to insert a femoral prosthesis 100 than to extract a femoral prosthesis 100.

The foregoing detailed description of one or more embodiments of the femoral prosthesis and instrument has been presented herein by way of example. It will be recognized that there are advantages to certain individual features and functions described herein that may be obtained without incorporating other features and functions described herein. Moreover, it will be recognized that various alternatives, modifications, variations or improvements of the above-disclosed embodiments and other features and functions, or alternatives thereof, may be desirably combined into many other different embodiments, systems or applications. Presently unforeseen or unanticipated alternatives, modifications, variations or improvements therein may be subsequently made by those skilled in the art which are also intended to be encompassed by the appended claims. Therefore, the spirit and scope of any appended claims should not be limited to the description of the embodiments contained herein.

What is claimed is:

1. A kit comprising a plurality of femoral prostheses of different sizes and shapes, each femoral prosthesis comprising:
   a femoral stem including a proximal end portion defining a proximal stem axis;
   a femoral neck portion located proximally of the proximal end portion, the femoral neck portion including a lateral shoulder extending distally and laterally from a proximal location of the neck at an angle relative to the proximal stem axis, such that when projected onto a coronal plane including the proximal stem axis, the lateral shoulder is not parallel to the proximal stem axis; and
   an insertion/extraction cavity extending distally from a proximal surface of the femoral neck portion and configured to couple with an insertion/extraction instrument, the cavity defining an insertion/extraction cavity axis which, when projected on to the coronal plane including the proximal stem axis, is not parallel with the proximal stem axis, wherein the lateral shoulder of each femoral prosthesis in the kit is oriented at an angle relative to the proximal stem axis that is different from the angle of each of the other femoral prostheses in the kit.

2. The kit of claim 1, wherein the angle of the insertion/extraction cavity axis relative to the proximal stem axis of each of the femoral prostheses in the kit is approximately equal to the angle of the lateral shoulder of the smallest femoral prosthesis in the kit relative to the proximal stem axis of the smallest femoral prosthesis in the kit.

3. The kit according to claim 2, wherein the angle of the lateral shoulder of the smallest femoral prosthesis in the kit relative to the proximal stem axis of the smallest femoral prosthesis in the kit is approximately 12°.

4. The kit of claim 3, wherein the insertion/extraction cavity of each of the femoral prostheses in the kit comprises a keyed portion configured to mate with a keyed portion of an insertion/extraction instrument.

5. The kit of claim 4, wherein the keyed portion of each of the femoral prostheses in the kit includes a keyed portion surface arranged substantially orthogonally relative to the insertion/extraction cavity axis.

6. The kit of claim 5, wherein the insertion/extraction cavity of each of the femoral prostheses in the kit includes a threaded portion configured to receive a threaded portion of the insertion/extraction instrument.

7. The kit of claim 3, further including an insertion/extraction instrument which includes a distal end portion configured to couple with the insertion/extraction cavity in each of the femoral prostheses in the kit.

8. The kit of claim 7, wherein the insertion/extraction instrument includes a shaft defining an axis which extends through the center of the shaft and through its opposite ends and is configured such that the axis of the shaft is parallel to and aligned with the insertion/extraction cavity axis of each of the femoral prostheses in the kit when the insertion/extraction instrument is coupled with of each of the femoral prostheses in the kit.

9. The kit of claim 8, wherein the shaft includes a proximal end portion configured as an impact surface and a threaded distal end portion configured to threadedly engage a threaded portion of the insertion/extraction cavity of each of the femoral prostheses in the kit.

10. The kit of claim 1, in which the angle of the insertion/extraction cavity axis relative to the proximal stem axis of each of the femoral prosthesis in the kit is approximately equal to the angle of the lateral shoulder of that femoral prosthesis relative to the proximal stem axis of that femoral prosthesis.

11. The kit of claim 1, wherein the insertion/extraction cavity of each of the femoral prostheses in the kit comprises a keyed portion configured to mate with a keyed portion of an insertion/extraction instrument.

12. The kit of claim 11, wherein the keyed portion of each of the femoral prostheses in the kit includes a keyed portion surface arranged substantially orthogonally relative to the insertion/extraction cavity axis.

13. The kit of claim 1, in which the stem of each of the femoral prostheses in the kit is substantially straight.

14. The kit of claim 1, wherein the proximal surface of the neck portion of each of the femoral prostheses in the kit in which the insertion/extraction cavity is provided extends parallel to a transverse plane which is perpendicular to the proximal stem axis of each of the femoral prostheses in the kit.

15. The kit of claim 1, further including an insertion/extraction instrument which includes a distal end portion configured to couple with the insertion/extraction cavity in each of the femoral prostheses in the kit.

16. The kit of claim 15, wherein the insertion/extraction instrument includes a shaft defining an axis which extends through the center of the shaft and through its opposite ends and is configured such that the axis of the shaft is parallel to and aligned with the insertion/extraction cavity axis of each of the femoral prostheses in the kit when the insertion/extraction instrument is coupled with of each of the femoral prostheses in the kit.

17. The kit of claim 16, wherein the shaft includes a proximal end portion configured as an impact surface and a threaded distal end portion configured to threadedly engage a threaded portion of the insertion/extraction cavity of each of the femoral prostheses in the kit.

* * * * *